United States Patent [19]

Engelhardt et al.

[11] Patent Number: 4,959,441

[45] Date of Patent: Sep. 25, 1990

[54] ALKENYLPHOSPHONIC AND -PHOSPHINIC ACID ESTERS, PROCESS FOR THEIR PREPARATION, HYDROGELS PRODUCED USING THEM, AND THEIR USE

[75] Inventors: Friedrich Engelhardt; Ulrich Riegel, both of Frankfurt; Joachim Gersdorf, Wiesbaden; Hans-Jerg Kleiner, Kronberg, all of Fed. Rep. of Germany

[73] Assignee: Cassella Aktiengesellschaft, Frankfurt am Main, Fed. Rep. of Germany

[21] Appl. No.: 348,395

[22] Filed: May 8, 1989

[30] Foreign Application Priority Data

May 21, 1988 [DE] Fed. Rep. of Germany ....... 3817425

[51] Int. Cl.$^5$ .............................................. C07F 9/02
[52] U.S. Cl. ................................... 558/161; 558/164; 558/165
[58] Field of Search .................... 558/161, 164, 165

Primary Examiner—Mukund J. Shah
Attorney, Agent, or Firm—Connolly and Hutz

[57] ABSTRACT

Alkenylphosphonic and -phosphinic acid esters of 1,1,1-tris(hydroxymethyl)alkanes and of 2,2-bis-hydroxymethyl-1,3-propanediol are useful as cross-linking agents in polymeric hydrogels.

2 Claims, No Drawings

ALKENYLPHOSPHONIC AND -PHOSPHINIC ACID ESTERS, PROCESS FOR THEIR PREPARATION, HYDROGELS PRODUCED USING THEM, AND THEIR USE

The invention relates t novel alkenylphosphonic and—phosphinic acid esters of 1,1,1-tris(hydroxymethyl)alkanes and of 2,2-bis-hydroxymethyl-1,3-propanediol, a process for their preparation, hydrogels produced using them, and their use.

In the production of hydrogels in aqueous solution, the crosslinking agents customarily used are compounds such as bisacrylamidoacetic acid, trimethylolpropane triacrylate, tetraallyloxyethane or similar.

Surprisingly, it has been found that hydrogels having improved properties with respect to absorption capacity and gel strength are obtained if the crosslinking agents employed are compounds of the general formula I

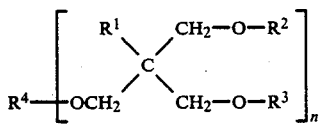
(I)

in which
n denotes 1 or 2
$R^1$ denotes alkyl having 1 to 4 carbon atoms, $CH_2OH$ or $CH_2OR^7$ in which $R^7$ can be defined as for $R^2$ or, if n=1, can form, together with $R^4$, a group of the general formula II

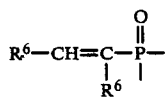
(II)

in which $R^6$, independently of one another, denote hydrogen or alkyl having 1 to 4 carbon atoms,
$R^2$ denotes a group of the general formula III

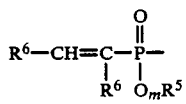
(III)

in which m denotes 0 or 1 and
$R^5$ denotes alkyl having 1 to 4 carbon atoms, where, if a compound of the general formula I contains more than one group of the general formula III, the radicals $R^5$ are independent of one another,
$R^3$ denotes hydrogen or a group of the general formula III, where $R^2$ and $R^3$ together may alternatively form a group of the general formula II,
$R^4$, where n=1, denotes hydrogen, a group of the general formula III or, if $R^1$ represents alkyl having 1 to 4 carbon atoms and $R^2$ and $R^3$ together represent a group of the general formula II, alternatively denotes a group of the general formula IV

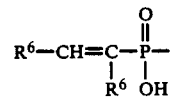
(IV)

and, where n=2, denotes a group of the general formula II.

Alkyl $R^1$ preferably has 1 or 2 carbon atoms.
Alkyl $R^5$ or $R^6$ preferably has 1 to 3 carbon atoms.
$R^6$ particularly preferably denotes methyl and very particularly preferably hydrogen.

Very particularly preferred compounds of the general formula I are the compounds of formulae V to XV

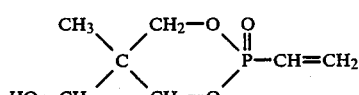
(V)

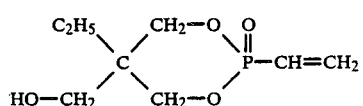
(VI)

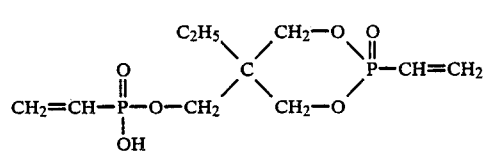
(VII)

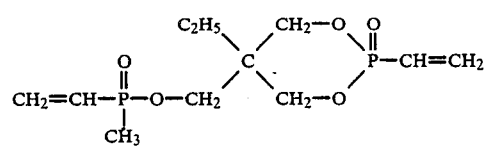
(VIII)

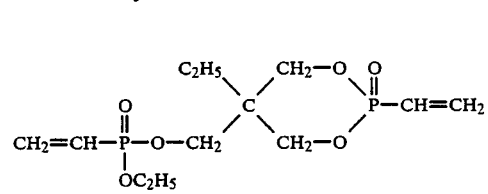
(IX)

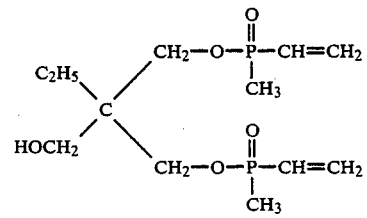
(X)

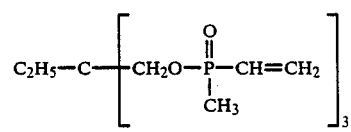
(XI)

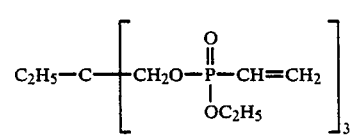
(XII)

-continued

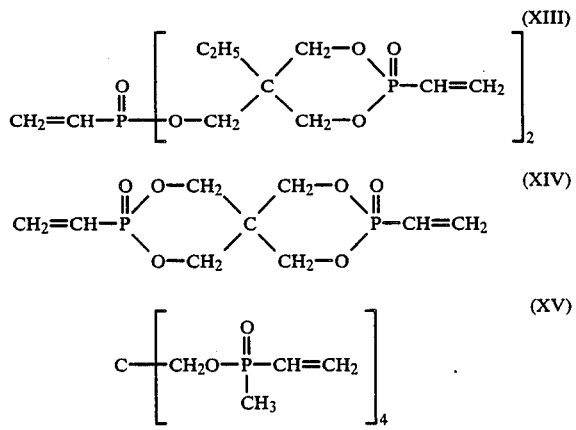

The compounds of the general formula I according to the invention can be prepared by various methods.

For example, alkenyldichlorophosphonic acids of the general formula XVI

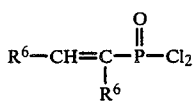

alkenylchlorophosphinic acids of the general formula XVII

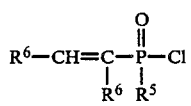

or alkenylchlorophosphonic acid esters of the general formula XVIII

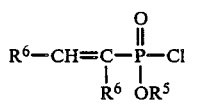

where $R^5$ and $R^6$ are as defined above, are reacted with 1,1,1-(trishydroxymethyl)alkanes, 2,2-bis-hydroxymethyl-1,3-propanediol or compounds of the general formula I according to the invention which also contain at least one free hydroxyl group, in the presence of tertiary amines as acid scavengers in inert solvents and at suitable molar ratios.

Suitable tertiary amines are, for example, trialkylamines having 1 to 4 carbon atoms per alkyl radical, such as, for example, triethylamine, dialkylanilines having 1 to 4 carbon atoms in the alkyl radical, such as, for example, N,N'-dimethylaniline, and pyridine.

Suitable inert solvents are, for example, halogenated hydrocarbons, such as, for example, methylene chloride, aromatic hydrocarbons, such as, for example, toluene, ethers, such as, for example, tetrahydrofuran, or aliphatic nitriles, such as, for example, acetonitrile.

The reactions preferably proceed with cooling at −10° to +40° C.

The tertiary amines are preferably employed in amounts of 1 mole per mole of HCl eliminated. The alcohol:organophosphorus compound molar ratios are preferably 1:1, 1:2, 1:3 or 1:4, depending on the coreactant and the desired product of the general formula I.

This method can be used to produce, for example, compounds of the type of the formula VI starting from an alkenyldichlorophosphonic acid of the general formula XVI, a 1,1,1-(trishydroxymethyl)alkane and a tertiary amine in the molar ratio 1:1:2, compounds of the type of the formula XI starting from an alkenylchlorophosphinic acid of the general formula XVII, a 1,1,1-(trishydroxymethyl)alkane and a tertiary amine in the molar ratio 3:1:3, and compounds of the type of the formula XII starting from an alkenylchlorophosphonic acid ester of the general formula XVIII, a 1,1,1-(trishydroxymethyl)alkane and a tertiary amine in the molar ratio 3:1:3.

If desired, the compounds according to the invention obtained in this way, which still contain free hydroxyl groups, can be reacted with alkenylphosphonic anhydrides, alkenylchlorophosphinic acids of the general formula XVII, alkenylchlorophosphonic acid esters of the general formula XVIII or alkenyldichlorophosphonic acids of the general formula XVI to form further compounds according to the invention. These reactions are carried out under the same conditions as described above.

Thus, for example, starting from the compound of the type of the formula VI, compounds of the type of the formula VII are obtained by reaction with an alkenylphosphonic anhydride, compounds of the type of the formula VIII are obtained by reaction with an alkenylchlorophosphinic acid and a tertiary amine in the molar ratio 1:1:1, compounds of the type of the formula IX are obtained by reaction with an alkenylchlorophosphonic acid ester and a tertiary amine in the molar ratio 1:1:1, and compounds of the type of the formula XIII are obtained by reaction with an alkenyldichlorophosphonic acid and a tertiary amine in the molar ratio 2:1:2.

Compounds of general the formula I according to the invention can also be obtained by direct esterification of alkenylphosphonic acids of the general formula XIX

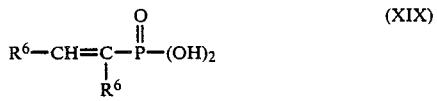

or of alkenylphosphinic acids of general formula XX

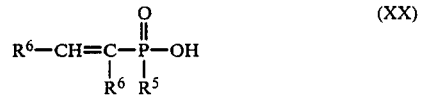

in which $R^5$ and $R^6$ are as defined above, using 1,1,1-(trishydroxymethyl)alkanes or 2,2-bis-hydroxymethyl-1,3-propanediol.

The alkenyl acids of phosphorus and the alcohol are advantageously mixed here in the desired molar ratio and reacted at temperatures of from 150° to 250° C., preferably 160° to 220° C., with elimination of water. Here too, the alcohol:acid molar ratios are preferably 1:1, 1:2, 1:3 or 1:4, depending on the coreactant and the desired product of the general formula I. If appropriate, the reaction can be carried out in a suitable vacuum.

It may be expedient to add certain known polymerization inhibitors, such as, for example, hydroquinne, hydroquinone monomethyl ether or phenothiazine. It may also be advantageous not to carry out the esterification to completion, but instead to terminate it at a certain residual acid content, since, otherwise, the reaction duration must be extended excessively and, in addition, polymerization of the reaction material cannot always be prevented under these conditions.

Finally, compounds of the general formula I according to the invention can also be obtained by reacting alkenylphosphonic acid esters of the general formula XXI

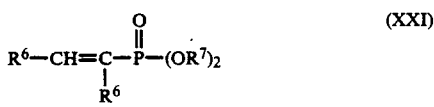

or alkenylphosphinic acid esters of the general formula XXII

in which $R^5$ and $R^6$ are as defined above and $R^7$ denotes alkyl having 1 to 4 carbon atoms, with 1,1,1-(trishydroxymethyl)alkanes or 2,2-bis-hydroxymethyl-1,3-propanediol with the aid of suitable catalysts.

Suitable catalysts are, for example, alkali metal alcoholates or alkali metal hydrides, such as sodium hydride, ortho-titanic acid esters, such as, for example, tetraisopropyl ortho-titanate, but also alkaline metal hydroxides, such as, for example, potassium hydroxide and sodium hydroxide.

The esterification reactions are preferably carried out in vacuo in the temperature range 150°–250° C., preferably 180°–220° C. The molar ratios are preferably selected analogously to the direct esterification.

Some of the products produced in the processes indicated can be purified in a high vacuum by distillation, in particular with the aid of a thin-film evaporator. However, some of them can also be processed further directly as the crude product.

2,2-Bis-hydroxymethyl-1,3-propanediol is a commercially available compound. 1,1,1-(Trishydroxymethyl)alkanes preferably have 5 to 8, particularly preferably 5 or 6, carbon atoms. They are likewise commercially available or can be prepared by known methods (for example Houben-Weyl, Methoden der Organischen Chemie, Georg Thieme Verlag, Stuttgart, Vol. 6/1a/2, 1980, page 1314).

The organophosphorus compounds of the general formulae XVI to XXII mentioned as starting materials for the synthesis of the compounds of the general formula I are likewise commercially available or accessible by customary methods (for example Houben-Weyl, Methoden der Organischen Chemie, Georg Thieme Verlag, Stuttgart, Vol. 12/1, 1963, pages 217 ff and 338 ff).

The compounds of the general formula I according to the invention which contain at least two double bonds are used as so-called crosslinking agents, i.e. polymerizable, polyunsaturated monomers, in the synthesis of polymers, in particular water-swellable hydrogels, from unsaturated monomers. An essential advantage here is their very good solubility both in polar and in non-polar solvents. Thus, the compounds of the general formula I, in contrast to, for example, trimethylolpropane triacrylate or trimethylolpropane trimethacrylate, are infinitely miscible with water. In addition, they are non-volatile, low-odour substances. This results in the further advantage of a substantially reduced tendency towards diffusion or evaporation during the polymerization process.

Compounds of the general formula I according to the invention which contain at least one free hydroxyl group can also be used as a starting compound for a synthesis of further compounds according to the invention.

The present invention also relates to water-swellable hydrogels which can be prepared by copolymerization of hydrophilic monomers and are characterized in that compounds of the general formula I are employed as crosslinking agents in the copolymerization.

Suitable hydrophilic monomers are, in particular, acrylic acid, methacrylic acid, crotonic acid, 2-acrylamide-2-methylpropanesulphonic acid and -phosphonic acid, vinylphosphonic acid, vinylphosphonic acid semiesters, salts thereof, acrylamide, N-vinylamides or mixtures thereof. Acrylic acid and salts thereof are preferred.

The compounds of the general formula I are preferably employed in amounts of from 0.05 to 20% by weight, based on the total monomer weight.

The polymerization can be carried out in the homogeneous phase, for example in aqueous solution, as a so-called gel polymerization or by the process of inverse emulsion polymerization. A further way of synthesizing the hydrogels according to the invention is by precipitation polymerization from organic solvents, such as, for example, alcohols, preferably tert. butanol, or hydrocarbons, such as hexane or cyclohexane.

The polymerization can be initiated by free-radical formers, such as, for example, organic or inorganic peroxides and azo compounds. Examples are benzoyl peroxide, tert. butyl hydroperoxide, cumene hydroperoxide, $(NH_4)_2S_2O_8$, $K_2S_2O_8$, $H_2O_2$ or azodiisobutyronitrile. Redox systems are also highly suitable polymerization initiators.

Finally, the polymerization can also be initiated by high-energy radiation.

The hydrogels according to the invention are highly suitable as absorbents for aqueous liquids, for the formulation of cosmetic preparations, and as additives in drilling muds and cement slurries in oil recovery.

Copolymers of acrylic acid and the compounds of the general formula I according to the invention behave particularly advantageously as so-called super absorbing polymers (SAP) when used in hygiene articles, such as, for example, nappies, it being possible for part of the acrylic acid to be in the form of an alkali metal salt or ammonium salt. The neutralization can be carried out either before or after the polymerization.

Compared to the compounds of the prior art, the water-swellable hydrogels according to the invention are distinguished by a more homogeneous network structure, since the compounds of the general formula I according to the invention are completely soluble both in water and in polar organic solvents. This means that the hydrogels have high absorption capacities as well as a high gel strength.

Examples 1 to 12 below illustrate the present invention with respect to the compounds of the general formula I, and Examples 13 to 34 with respect to the hydrogels.

EXAMPLE 1

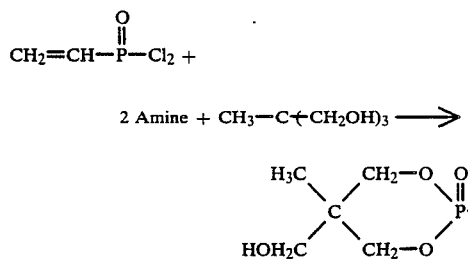

(V)

240 g (2.0 mol) of 1,1,1-(trishydroxymethyl)ethane and 404 g (4.0 mol) of triethylamine are introduced into 1600 ml of tetrahydrofuran. 290 g (2.0 mol) of vinyldichlorophosphonic acid are added dropwise at 20° C. over the course of 2 hours with vigorous stirring and with cooling. The mixture is then stirred for a further 15 hours, the triethylamine hydrochloride formed is subsequently filtered off with suction and washed with tetrahydrofuran, and the filtrate is freed from tetrahydrofuran by distillation in vacuo. The residue is distilled by means of a thin-film evaporator at 0.067 kPa and a bath temperature of 240° C. 345 g are obtained, m.p.: 70°–75° C. The boiling point is determined by a distillation experiment: 213°–215° C./0.053 kPa. The product is produced as a diastereomer mixture. The yield is 90% of theory.

$C_7H_{13}O_4P$ (192):
 cal.: 43.75%, C 6.77%, H 16.15% P.
 found: 43.6%, C 6.8%, H 16.1% P.

EXAMPLE 2

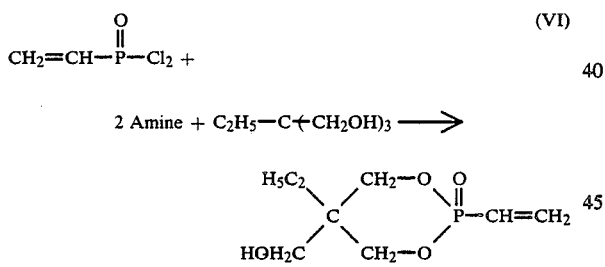

(VI)

280 g (2.09 mol) of 1,1,1-(trishydroxymethyl)propane and 422 g (4.18 mol) of triethylamine are dissolved in 1600 ml of tetrahydrofuran. 303 g (2.09 mol) of vinyldichlorophosphonic acid are then added dropwise at 20° C. over the course of 3 hours with vigorous stirring and with cooling. The mixture is stirred for a further 15 hours, the triethylamine hydrochloride formed is subsequently filtered off with suction and washed with tetrahydrofuran, and the filtrate is freed from tetrahydrofuran by distillation in vacuo. The residue is distilled by means of a thin-film evaporator at 0.027 kPa and a bath temperature of 240° C. 370 g are obtained, and the product has a solidification point of about 25° C. The boiling point is determined by a distillation experiment: 199° C./0.013 kPa. $n_0^{20}$: 1.4890. The product is produced as a diastereomer mixture. The yield is 86% of theory.

$C_8H_{15}O_4P$ (206):
 calc.: 46.60%, C 7.28%, H 15.05% P.
 found: 46.4%, C 7.3%, H 14.8% P.

EXAMPLE 3

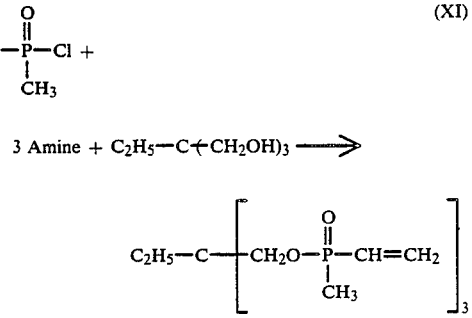

(XI)

20 g (0.15 mol) of 1,1,1-(trishydroxymethyl)propane and 45.5 g (0.45 mol) of triethylamine are introduced into 150 ml of toluene. 56 g (0.45 mol) of methylvinylchlorophosphinic acid are added dropwise at 20° C. with vigorous stirring and with cooling. The mixture is then stirred for a further 15 hours, the triethylamine hydrochloride formed is subsequently filtered off with suction and washed with toluene, and the filtrate is freed from toluene by distillation in vacuo. 58 g of the product having a refractive index $n_0^{20} = 1.4942$ remain. The products can be distilled by means of a thin-film evaporator at 0.027 kPa and a bath temperature of 260°–270° C. The yield of the crude product is 97% of theory.

$C_{15}H_{29}O_6P_3$ (398):
 calc.: 23.37% P.
 found: 23.1% P.

EXAMPLE 4

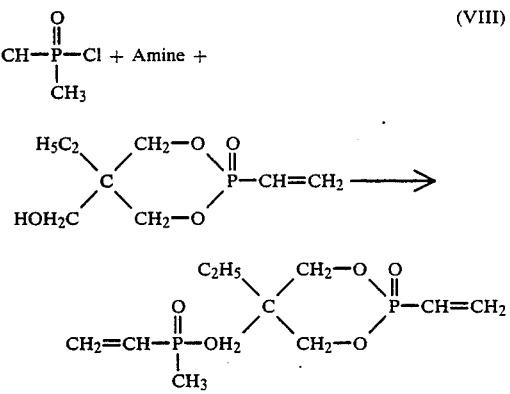

(VIII)

76 g (0.34 mol) of the compound of Example 2 and 34.4 g (0.34 mol) of triethylamine are introduced into 100 ml of tetrahydrofuran. 42.5 g (0.34 mol) of methylvinylchlorophosphinic acid are then added dropwise at 20° C. with vigorous stirring and with cooling. The mixture is then stirred for a further 15 hours, the triethylamine hydrochloride formed is subsequently filtered off with suction and washed with tetrahydrofuran, and the filtrate is freed from tetrahydrofuran by distillation in vacuo. 95 g of the compound VIII remain. The boiling point is determined by a distillation experiment: 205°–210° C./ 0.067 kPa. The yield of the crude product is 95% of theory.

$C_{11}H_{20}O_5P_2$ (294):
 calc.: 21.09% P.
 found: 20.5% P.

EXAMPLE 5

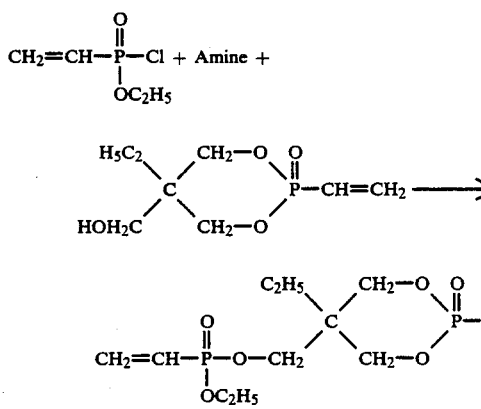
(IX)

34.7 g (0.168 mol) of the compound of Example 2 and 17 g (0.168 mol) of triethylamine are introduced into 100 ml of toluene. 26 g (0.168 mol) of ethyl vinylchlorophosphonate are then added dropwise at 20° C. with stirring and cooling. Stirring is continued, and the mixture is filtered with suction. After the solid material has been rinsed with toluene, the filtrate is freed from the solvent in vacuo. 52.5 g of the compound IX, $n_o^{20}=1.4848$, remain. The product can be distilled in a thin-film evaporator at 0.027 kPa and a bath temperature of 240° C. The yield of crude product is 96% of theory.

$C_{12}H_{22}O_6P_2$ (324):
calc.: 19.13% P.
found: 18.7% P.

EXAMPLE 6

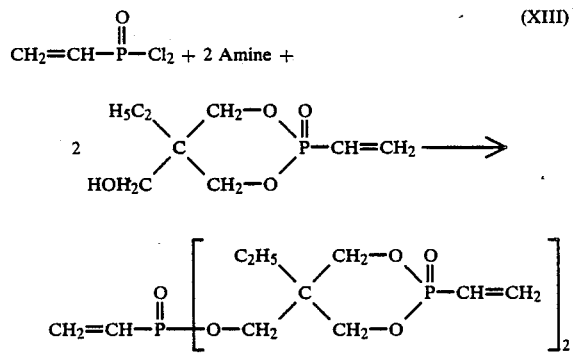
(XIII)

81.4 g (0.4 mol) of the compound of Example 2 and 40.4 g (0.4 mol) of triethylamine are introduced into 100 ml of toluene. 29 g (0.2 mol) of vinyldichlorophosphonic acid are then added dropwise at 20° C. with stirring and cooling. Stirring is continued, the mixture is filtered with suction, and the solid material is washed with toluene. The filtrate is freed from toluene in vacuo. 97 g of the product having the refractive index of $n_o^{20}=1.4945$ remain. This corresponds to a yield of 100% of theory.

$C_{18}H_{31}O_9P_3$ (484):
calc.: 19.21% P.
found: 19.2% P.

EXAMPLE 7

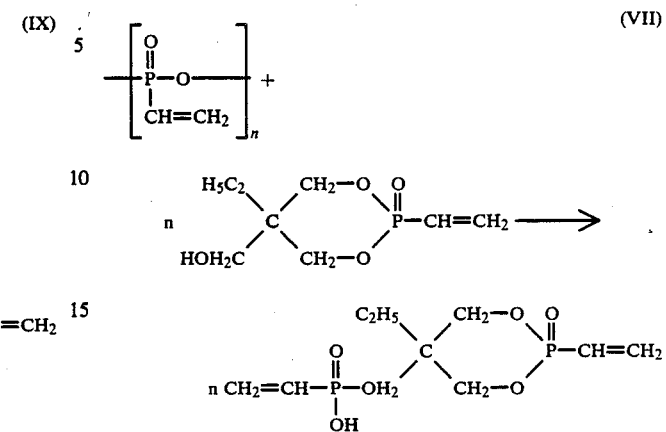
(VII)

321.4 g (1.56 mol) of the compound of Example 2 are dissolved in 321.4 g of methylene chloride. 280.8 g (0.2 mol) of a 50% strength solution of vinylphosphonic anhydride in methylene chloride are added dropwise over the course of one hour with stirring. During this addition, the temperature increases to 33° C., where it remains for 30 minutes. The mixture is then stirred for a further 3 hours and subsequently refluxed for a further 4 hours. The solvent is subsequently removed by distillation in vacuo over the course of about 3 hours up to an internal temperature of 50° C. 130 g of a crude product remain. The crude product has a refractive index $n_o^{20}=1.4945$. On the basis of a $^{31}P$ NMR spectrum, the product is a mixture of two diastereomers, which make up about 60% of the crude product ($d_6$-DMSO; $\delta=14.79$; 14.82; 11.78; 12.73 ppm). The starting material, the compound of Example 2, makes up 8% of the mixture, vinylphosphonic acid makes up 9% and vinylpyrophosphonic acid makes up 4%. $C_{10}H_{18}O_6P_2$ (296)

EXAMPLE 8

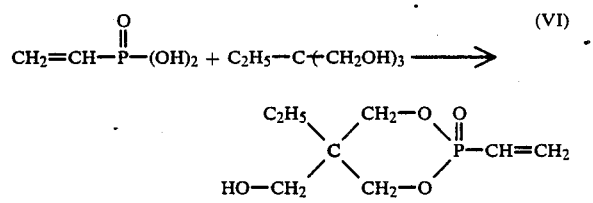
(VI)

53.7 g (0.4 mol) of 1,1,1-(trishydroxymethyl)propane and 43.2 g (0.4 mol) of vinylphosphonic acid are warmed to 160°-170° C. at 0.067 to 0.133 kPa with stirring. As the vacuum decreases, water collects in a cold trap downstream of the reaction apparatus. Where about 7.5 g of water have collected, the reaction temperature is increased to 200° C. and the vacuum is improved again, and the mixture is kept at this temperature for one hour. The reaction material produced now has an acid number of 134 mg of KOH/g of substance. The reaction material is subsequently distilled in a thin-film evaporator at 0.067 to 0.133 kPa and a bath temperature of 270° C. The product produced has an acid number of 38 mg of KOH/g of substance and a content of 76% on the basis of the $^{31}P$ NMR spectrum.

EXAMPLE 9

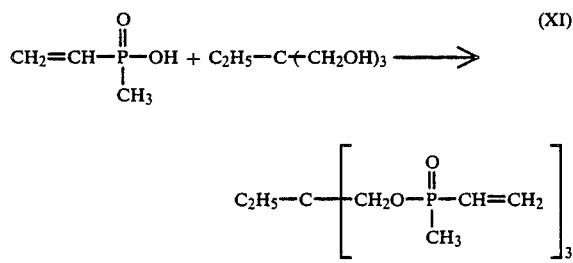

33.6 g (0.25 mol) of 1,1,1-(trishydroxymethyl)propane and 79.5 g (0.75 mol) of methylvinylphosphinic acid are heated to 150° C. at 0.067 to 0.133 kPa with vigorous stirring and then stepwise over the course of several hours to 190°–195° C. 12 g of water collect in a cold trap downstream of the reaction apparatus. The reaction material produced has an acid number of 134 mg of KOH/g of substance. The product is distilled in a thin-film evaporator at 260°–270° C. and 0.133 kPa. 81 g of product having a content of about 70% on the basis of the $^{31}$P NMR spectrum are obtained.

EXAMPLE 10

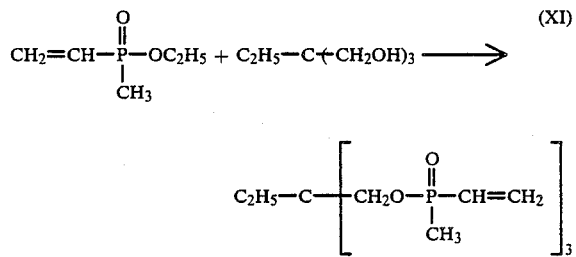

23.5 g (0.175 mol) of 1,1,1-(trishydroxymethyl)propane, 70.4 g (0.525 mol) of ethyl methylvinylphosphinate and 2.3 g of tetraisopropyl ortho-titanate are heated at 150° C. and then in steps over the course of several hours and with vigorous stirring to 210° C. A total of 12 g of ethanol are distilled off. The reaction material produced has an acid number of 75 mg of KOH/g of substance. It can be distilled in a thin-film evaporator at 0.053 kPa and a bath temperature of 250°–260° C.

EXAMPLE 11

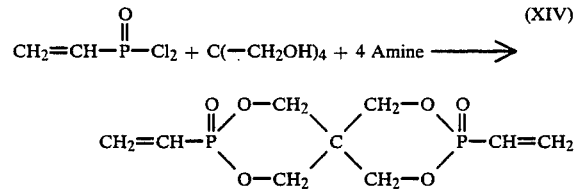

68.1 g (0.5 mol) of 2,2-bis-(hydroxymethyl)-1,3-propanediol are introduced into 400 ml of acetonitrile, and 202.4 g (2.0 mol) of triethylamine are added dropwise to the mixture with stirring. 145 g (1 mol) of vinyldichlorophosphonic acid are then added dropwise at 30° C., and the mixture is stirred for a further 15 hours. The mixture is then heated to reflux and, after about 15 minutes, filtered with suction while hot. Crystals again deposit from the filtrate and are likewise filtered off with suction, a total of about 265 g of triethylamine hydrochloride being obtained. The acetonitrile is then removed from the filtrate by distillation, and the residue is digested with acetone. 125 g of crude product are obtained, and are recrystallized from isopropanol, m.p.: 161° C. The yield of crude product is about 90% of theory.

$C_9H_{14}O_8P_2$ (280): calc.: 38.57%, C 5.0%, H 22.14% P. found: 38.3%, C 4.8%, H 21.0% P.

EXAMPLE 12

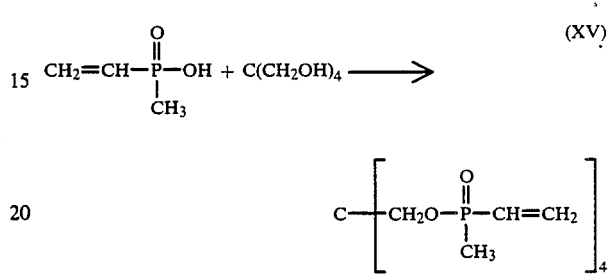

13.6 g (0.1 mol) of 2,2-bis-(hydroxymethyl)-1,3-propanediol and 42.4 g (0.4 mol) of methylvinylphosphinic acid are heated in steps over the course of about 5 hours to 155 to 190° C. and about 0.067 kPa with vigorous stirring. About 6 g of water collect in a cold trap downstream of the reaction apparatus. The crude product which is used has an acid number of 115 mg of KOH/g of substance. The refractive index is $n_D^{20} = 1.4911$.

$C_{78}H_{32}O_8P_4$ (488): calc.: 25.41% P. found: 24.2% P.

EXAMPLE 13

5,500 g of demineralized water are introduced into a polyethylene vessel with a capacity of 10 l which is well insulated by foamed plastic material, 1,740 g of sodium bicarbonate are dispersed therein, and 1,985 g of acrylic acid are added slowly at a rate such that overfoaming of the reaction solution is avoided, the reaction solution cooling to a temperature of about 10°–8° C. 15 g of the compound VII according to the invention, prepared in accordance with Example 7, and 10 g of a sodium diisoctylsulphosuccinate (Rewopol V 2133 from Messrs. REWO, Steinau) are then added. The initiators, a redox system, comprising 6 g of potassium peroxydisulphate, dissolved in 170 g of water, and 0.2 g of ascorbic acid, dissolved in 20 g of water, are added successively at a temperature of 1°–10° C., and the mixture is stirred well. The reaction solution is then left to stand without stirring, a solid gel being produced by polymerization setting in, during which the temperature increases to about 85° C. The gel is subsequently comminuted mechanically, dried at temperatures above 80° and ground.

The above-described product is incorporated in a customary manner into a baby nappy, and is distinguished here by particularly good liquid retention.

EXAMPLE 14

4,290 g of ice and 1,970 g of acrylic acid are introduced into a 10 liter plastic vessel, and 1,655 g of 50% strength NaOH are slowly added, followed by 30 g of the compound VII according to the invention, prepared in accordance with Example 7, dissolved in 100 g of water, and 10 g of Rewopol V 2133. The temperature of the reaction solution is adjusted to 20° C., the initiators, a redox system comprising 6 g of potassium peroxydisulphate, dissolved in 170 g of water, and 0.2 g of ascorbic acid, dissolved in 120 g of water, are subsequently added, and the mixture is left to stand without stirring. The gel produced by polymerization is subsequently comminuted mechanically, dried at temperatures above 80° C. and ground.

EXAMPLE 15

5,250 g of demineralized water, 1,988 g of acrylic acid and 12 g of the compound XIII according to the invention, prepared in accordance with Example 6, are introduced into a 10 liter polyethylene vessel, and 10 g of Rewopol V 2133 are stirred in. After the temperature of the reaction solution has been adjusted to 18°–20° C., the initiators, 6 g of potassium peroxydisulphate in 170 g of water and 0.2 g of ascorbic acid in 20 g of water are added successively, and the reaction mixture is left to stand without stirring and with good insulation. After the reaction has set in, the temperature increases to about 90° C., and a solid gel is produced. This is comminuted mechanically by means of an extruder, to which 1,555 g of 50% strength NaOH are metered continuously, some evaporation of the water occurring. The flocculent polymer is subsequently dried to completion at temperatures above 80° C. and ground.

EXAMPLE 16

5,380 g of demineralized water are introduced into a polyethylene vessel with a capacity of 10 l which is well insulated by foamed plastic material, 1,740 g of sodium bicarbonate are dispersed therein, and 1,985 g of acrylic acid are added slowly at a rate such that over-foaming of the reaction solution is avoided, the reaction solution cooling to a temperature of about 10°–8° C. 15 g of the compound XI according to the invention, prepared in accordance with Example 3, and 10 g of a sodium diisooctylsulphosuccinate (Rewopol V 2133 from Messrs. REWO, Steinau) are then added. At a temperature of 6°–8° C., the initiators, a redox system, comprising 2.2 g of 2,2'-azobisamidinopropane dihydrochloride, dissolved in 20 g of water, and 0.2 g of ascorbic acid, dissolved in 20 g of water, 4.4 g of potassium peroxydisulphate, dissolved in 170 g of water, and 6 g of sodium pyrosulphite, dissolved in 120 g of water, are added successively, and the mixture is stirred well. The reaction solution is then left to stand without stirring, a solid gel being produced due to polymerization setting in, during which the temperature increases to about 85° C. The gel is subsequently comminuted mechanically, dried at temperatures above 80° and ground.

The product described above is incorporated in a customary manner into a baby nappy and is distinguished here by particularly good liquid retention.

EXAMPLE 17

468 g of tert. butanol (600 ml) are introduced into a 1 liter glass polymerization flask equipped with stirrer, thermometer, reflux condenser, gas-inlet tube and water bath, and 0.1 g of the compound V according to the invention, prepared in accordance with Example 1, and 65 g of APS are suspended therein with stirring. 5.5 g of ammonia gas are then introduced via the gas-inlet tube, a slightly turbid solution being produced. The pH of this solution must be >7. 15 g of acrylamide and 20 g of N-vinyl-N-methylacetamide are then added, and the solution is heated to a temperature of 50° C. while a gentle stream of nitrogen is passed in. 1.0 g of POROFOR N is then added. The stirrer speed is reduced to 60–80 rpm, and the passing-in of the nitrogen stream is continued. After about 20 minutes, the polymerization sets in, which can be detected from flocculation of the polymer at a slight temperature increase. A thick, just stirrable slurry is produced over the course of about 1 hour, and the temperature increases to a maximum of 70° C. After the temperature maximum has been reached, the mixture is stirred for 2 hours at a bath temperature of 80° C. The reflux condenser is now replaced by a distillation bridge, and, after the mixture has been cooled to 60° C., the tert. butanol is removed by distillation under a water-pump vacuum. The finished product obtained is 105 g of a white powder having a bulk density of about 0.2 kg/l and which is highly suitable as an additive in drilling muds and cement slurries in the recovery of oil.

EXAMPLE 18

600 ml of hexane are introduced into a 1 liter glass polymerization flask equipped with stirrer, thermometer and reflux condenser, and 98.9 g of acrylic acid and 1.1 g of the compound XIII according to the invention, prepared in accordance with Example 6, are dissolved therein. While a gentle stream of $N_2$ is passed in, the mixture is heated to 68° C. by means of an electrically heated water bath, and 1.0 g of dilauryl peroxide is then added. After the polymerization has set in, a significant reflux occurs, and the polymer produced flocculates. The mixture is stirred for a further 3 hours under reflux, and the polymer is then filtered off with suction and dried to constant weight in a drying oven. 100 g of a white powder which can be employed as an acid thickener in cosmetic preparations are obtained.

Further examples of the preparation of polymers according to the invention in accordance with Examples 13 to 18 described here are collated in Table 1 below. The amounts given denote percent by weight, based on a total amount of monomer.

The following abbreviations are used:
AA: acrylic acid
MAA: methacrylic acid
CTA: crotonic acid
VPA: vinylphosphonic acid
VPE: vinylphosphonic acid semiester
APA: 2-acrylamido-2-methylpropanesulphonic acid
AMPP: 2-acrylamido-2-methylpropanephosphonic acid
AM: acrylamide
VIMA: N-vinyl-N-methylacetamide.

TABLE 1

| Example | Prepared analogously to example | AA % | MAA % | APA % | AMPP % | VPA % | VPE % | CTA % | AM % | VIMA % | Compound to the Formula | according invention According to example | % | Degree of neutralization |
|---|---|---|---|---|---|---|---|---|---|---|---|---|---|---|
| 19 | 16 | 79.25 | | 20.00 | | | | | | | 4 | 4 | 0.75 | 75 |
| 20 | 14 | 98.50 | | | | | | | | | 10 | 11 | 1.50 | 75 |
| 21 | 16 | 99.50 | | | | | | | | | 11 | 12 | 0.50 | 50 |

TABLE 1-continued

| Example | Prepared analogously to example | AA % | MAA % | APA % | AMPP % | VPA % | VPE % | CTA % | AM % | VIMA % | Compound to the Formula | according invention According to example | % | Degree of neutralization |
|---|---|---|---|---|---|---|---|---|---|---|---|---|---|---|
| 22 | 15 | 99.25 | | | | | | | | | 3 | 7 | 0.75 | 65 |
| 23 | 13 | 99.25 | | | | | | | | | 5 | 5 | 0.75 | 65 |
| 24 | 16 | 80.0 | 10.0 | 9.5 | | | | | | | 6 | | 0.5 | 48 |
| 25 | 16 | 70.0 | | 25.0 | | 4.0 | | | | | 3 | 7 | 1.0 | 75 |
| 26 | 16 | 75.0 | | 20.0 | | | 4.0 | | | | 3 | 7 | 1.0 | 75 |
| 27 | 16 | 85.0 | 10.0 | | | | 4.0 | | | | 7 | 3 | 1.0 | 70 |
| 28 | 16 | 40.0 | | 25.0 | 4.0 | | | | 30.0 | | 8 | | 1.0 | 80 |
| 29 | 15 | 75.0 | | 19.3 | | | | 5.0 | | | 11 | 12 | 0.7 | 55 |
| 30 | 15 | 95.0 | | | 4.6 | | | | | | 11 | 12 | 0.4 | 45 |
| 31 | 13 | 85.0 | | 10 | 4.5 | | | | | | 7 | 3 | 0.5 | 70 |
| 32 | 14 | 97.4 | | | | | | | | | 4 | 4 | 2.6 | 80 |
| 33 | 17 | | | 60 | | | | | 15 | 20 | 1 | 1 | 5.0 | 100 |
| 34 | 17 | | | 45 | | | | | 15 | 20 | 2 | 2 | 20.0 | 100 |

What is claimed is:

1. Compounds of the formula (I)

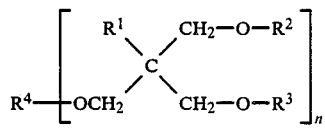

in which
n denotes 1 or 2
$R^1$ denotes alkyl having 1 to 4 carbon atoms, $CH_2OH$ or $CH_2OR^7$ in which $R^7$ is as defined for $R^2$ or, when n is 1, $R^2$ is together with $R^4$, moiety of the formula (II)

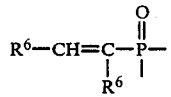

in which $R^6$, independently of one another, denote hydrogen or alkyl having 1 to 4 carbon atoms,
$R^2$ denotes the formula (III)

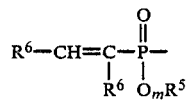

in which m denotes 0 or 1 and
$R^5$ denotes alkyl having 1 to 4 carbon atoms, where, if a compound of the formula I contains more than one of formula III, each $R^5$ is independent of one another,
$R^3$ denotes hydrogen or a moiety of formula (III), or $R^2$ and $R^3$ together form a moiety of formula (II), where n is 1, $R^4$ denotes hydrogen, a moiety of formula (III) or, when $R^1$ represents alkyl having 1 to 4 carbon atoms and $R^2$ and $R^3$ together are a moiety of the formula (II), $R^4$ denotes a moiety of the general formula (IV)

$$R^6-CH=C-\underset{\underset{OH}{|}}{\overset{\overset{O}{\|}}{P}}- \quad (IV)$$
$$\phantom{R^6-CH=}\underset{R^6}{|}$$

and, when n is 2, $R^4$ denotes a moiety of the formula (II).

2. Compounds according to claim 1 wherein $R^6$ denotes hydrogen.

* * * * *